(12) United States Patent
Yu et al.

(10) Patent No.: US 10,989,727 B2
(45) Date of Patent: Apr. 27, 2021

(54) APPARATUS FOR CUP LOADING AND UNLOADING AND THROMBOELASTOGRAPHY MACHINE

(71) Applicant: Medcaptain Medical Technology Co., Ltd, Shenzhen (CN)

(72) Inventors: Zhiguang Yu, Shenzhen (CN); Shuai Yin, Shenzhen (CN); Lintao Wu, Shenzhen (CN); Jun Dong, Shenzhen (CN)

(73) Assignee: MEDCAPTAIN MEDICAL TECHNOLOGY CO., LTD, Shenzhen (CN)

( * ) Notice: Subject to any disclaimer, the term of this patent is extended or adjusted under 35 U.S.C. 154(b) by 331 days.

(21) Appl. No.: 16/256,269

(22) Filed: Jan. 24, 2019

(65) Prior Publication Data

US 2019/0170779 A1  Jun. 6, 2019

Related U.S. Application Data

(63) Continuation of application No. PCT/CN2018/085939, filed on May 8, 2018.

(30) Foreign Application Priority Data

May 15, 2017 (CN) .......................... 201710340936.2

(51) Int. Cl.
  *G01N 35/04* (2006.01)
  *G01N 33/86* (2006.01)
  *G01N 33/49* (2006.01)

(52) U.S. Cl.
  CPC ............ *G01N 35/04* (2013.01); *G01N 33/86* (2013.01); *G01N 33/4905* (2013.01); *G01N 2035/041* (2013.01); *G01N 2035/0427* (2013.01)

(58) Field of Classification Search
  CPC .. G01N 35/04; G01N 33/86; G01N 2035/041; G01N 33/4905;
  (Continued)

(56) References Cited

U.S. PATENT DOCUMENTS 5,223,227 A     6/1993 Zuckerman
5,777,215 A *   7/1998 Calatzis ............. G01N 33/4905
                                                     356/39

(Continued)

FOREIGN PATENT DOCUMENTS

CA     104614539 A    5/2015
CN       1784604      6/2006
(Continued)

OTHER PUBLICATIONS

International search report issued in corresponding international application No. PCT/CN2018/085939 dated Aug. 1, 2018.

*Primary Examiner* — Benjamin R Whatley
*Assistant Examiner* — John McGuirk
(74) *Attorney, Agent, or Firm* — Fish IP Law, LLP

(57) ABSTRACT

An apparatus for cup loading and unloading and a thromboelastography machine are provided. The apparatus for cup loading and unloading includes a base, a shaft, a movable cover, and a cup holder. The shaft is rotatably connected to the base about an axis of the shaft and has an end configured to engage with an inner cup. The movable cover is disposed around the shaft and slidably connected to the base along the axis of the shaft. The movable cover is provided with an elastic member therein. The cup holder is slidably connected to the base along the axis of the shaft and disposed below the base and the shaft. The cup holder has a cavity configured to engage with an outer cup, and the cavity has an open directed upward.

21 Claims, 3 Drawing Sheets

(58) Field of Classification Search
CPC ......... G01N 2035/0427; G01N 11/162; G01N 11/167; G01N 11/14; B29C 33/442; B29C 2045/1629; B29C 45/40; B29C 45/4005; B29C 2045/4063; B29C 2045/4094; B29C 49/70; B29C 2049/701; B29C 51/44; B29C 2045/7221
See application file for complete search history.

(56) References Cited

U.S. PATENT DOCUMENTS

| | | | |
|---|---|---|---|
| 2001/0053552 A1 | 12/2001 | Cohen et al. | |
| 2010/0154520 A1 | 6/2010 | Schubert | |
| 2019/0072470 A1* | 3/2019 | Yu | ........................... G01N 33/48 |

FOREIGN PATENT DOCUMENTS

| | | | |
|---|---|---|---|
| CN | 202501994 U | 10/2012 |
| CN | 104181311 A | 12/2014 |
| CN | 205449987 U | 8/2016 |
| CN | 106053590 A | 10/2016 |
| CN | 206990618 U | 2/2018 |

* cited by examiner

APPARATUS FOR CUP LOADING AND UNLOADING AND THROMBOELASTOGRAPHY MACHINE

CROSS-REFERENCE TO RELATED APPLICATIONS

The present application is a continuation of PCT/CN2018/085939, filed on May 8, 2018, which claims priority to Chinese Patent Application No. 201710340936.2, filed on May 15, 2017, the disclosures of which are hereby incorporated by reference in their entireties.

TECHNICAL FIELD

The present disclosure relates to a medical device for measuring thromboelastography, and particularly to an apparatus for cup loading and unloading and a thromboelastography machine.

BACKGROUND

Before a reaction test of a thromboelastography machine, a reaction cup needs to be loaded. The reaction cup includes an inner cup and an outer cup. During the reaction test, the inner cup is secured at an upper side, and the outer cup is secured at a lower side. Meanwhile, a certain gap between the inner cup and the outer cup needs to be maintained. The process of loading the reaction cup generally includes the following steps. Put the inner cup and outer cups of the reaction cup on a cup holder. Move the cup holder to a test position. Push up a loading device disposed in the cup holder to load the inner cup of the reaction cup. Move the cup holder down to a very bottom. Press down the outer cup of the reaction cup to load the outer cup. With those steps, the loading of the reaction cup is completed. It can be seen that the above-described process of loading the reaction cup are cumbersome, and the loading device needs to be provided for loading the inner cup, resulting in that the structure of the thromboelastography machine is complex. In addition, generally, the outer cup of the reaction cup is directly pressed down by hand, such that the reaction cup is prone to be contaminated, which may cause deviation of test results.

SUMMARY

The present disclosure provides an apparatus for cup loading and unloading and a thromboelastography machine, which can simplify loading process, thereby facilitating operations and avoiding contamination of the reaction cup.

In order to resolve the above-mentioned problem, according to an aspect of the present disclosure, an apparatus for cup loading and unloading is provided. The apparatus includes a base, a shaft, a movable cover, a cup holder, and a cup ejection assembly. The shaft is rotatably connected to the base about an axis of the shaft and has an end configured to engage with an inner cup. The movable cover is disposed around the shaft and slidably connected to the base along the axis of the shaft, and the movable cover is provided with an elastic member therein. The cup holder is slidably connected to the base along the axis of the shaft and disposed below the base and the shaft, the cup holder has a cavity configured to engage with an outer cup, and the cavity has an open directed upward.

The cup ejection assembly includes an ejection driving mechanism and an ejection block. The ejection block is slidably connected to the shaft along the axis of the shaft. The ejection driving mechanism is disposed between the base and the ejection block, and configured to provide a downward force on the ejection block. The elastic member is disposed between the ejection block and the movable cover, and configured to provide an upward force on the ejection block when in a deformation state.

When the cup holder slides upward to a contact position, the cup holder is in contact with a bottom end of the movable cover, and an upward movement of the cup holder drives the movable cover to slide upward. The elastic member is configured to provide a downward force on the movable cover when in a deformation state. An approach movement between the end of the shaft and the cup holder is configured to generate a force to engage the inner cup with the end of the shaft and to engage the outer cup within the cavity of the cup holder.

As one implementation, the ejection block is sleeved on the shaft, the elastic member is configured as a compression spring and sleeved on the ejection block, and the elastic member and the ejection block are disposed within the movable cover. The ejection block has an ejection flange disposed around a top portion of the ejection block, the movable cover has an annular flange circumferentially disposed on an inner wall of the movable cover, the ejection flange is disposed above the annular flange, and the elastic member has an end abutted against the ejection flange and another end abutted against the annular flange. A bottom portion of the ejection block is configured to move to pass through the annular flange to a position below the annular flange, when the ejection block is in a downward movement relative to the shaft.

As one implementation, the apparatus further includes a magnetic assembly. The magnetic assembly includes a first magnetic element fixedly connected to the cup holder and a second magnetic element fixedly connected to the bottom end of the movable cover, and the first magnetic element and the second magnetic element are attracted each other in a process of the cup holder and the movable cover approaching each other.

As one implementation, the cup holder is fixedly provided with a guiding rod in parallel with the shaft. The base has a guiding hole, and the guiding rod is slidably disposed through the guiding hole. A damper stop mechanism is disposed between the base and the guiding rod to allow the base and the guiding rod to be relatively fixed.

As one implementation, the damper stop mechanism includes a locking block and a locking spring. The locking block is slidably disposed in the base and is slidably movable in a direction perpendicular to an axis of the guiding rod. The locking spring is connected to the locking block and provides an elastic force on the locking block, whereby the locking block is abutted against the guiding rod.

As one implementation, the guiding rod includes two guiding rods disposed in parallel to and spaced apart from each other. The locking block includes two locking blocks. The locking spring is configured as a compression spring. The locking spring has two ends abutted against the two locking elements to provide a repulsive force on the two locking elements, whereby each of the two locking elements is abutted against one of the two guiding rods.

As one implementation, the cup holder is provided with a thermostat assembly configured to keep the outer cup at a constant temperature. The thermostat assembly includes a heater and a heating member, the heater is disposed around the heating member, and the cavity is defined in the heating member. The heater is integrated with a temperature sensor and a temperature protection switch.

As one implementation, the cup holder is further provided with a pushrod mechanism configured to eject the outer cup from the cavity. The pushrod mechanism includes a pushrod and a pushrod spring. The cup holder has a pushrod hole extending through a bottom surface of the cup holder and the cavity. The pushrod is slidably disposed through the pushrod hole along the axis of the shaft. The pushrod has a top portion configured to abut against the outer cup, and a bottom portion extending outside the pushrod hole and projecting from the bottom surface of the cup holder. The pushrod spring is connected to the pushrod and is configured to provide a downward force on the pushrod.

According to another aspect of the present disclosure, a thromboelastography machine is provided, which includes the above-mentioned apparatus for cup loading and unloading.

According to the apparatus for cup loading and unloading and the thromboelastography machine of the present disclosure, when pushing up the cup holder, the movable cover is forced to move upward, and the cup holder and the shaft are forced to move toward each other, so as to provide a force to engage the inner cup with the end of the shaft and to engage the outer cup within the cavity of the cup holder. Thus, the loading of the inner cup and the outer cup can be completed at one time. After loading, the movable cover slides downward under a force of the elastic member, so as to push down the cup holder to a test position. Steps for loading can be simplified, thereby facilitating operations. During the loading, there is no direct contact between a user and the reaction cup, thereby avoiding contamination of the reaction cup and ensuring the accuracy of test results.

BRIEF DESCRIPTION OF THE DRAWINGS

To describe the technical solutions in the implementations of the present disclosure or by the related art more clearly, the following briefly introduces the accompanying drawings required for describing the implementations or the related art. Apparently, the accompanying drawings in the following description illustrate some implementations of the present disclosure. Those of ordinary skill in the art may also obtain other drawings based on these accompanying drawings without creative efforts.

DETAILED DESCRIPTION OF ILLUSTRATED IMPLEMENTATIONS

Technical solutions in implementations of the present disclosure will be described clearly and completely hereinafter with reference to the accompanying drawings in the implementations of the present disclosure.

According to the implementations of the present disclosure, a thromboelastography machine is provided, which includes an apparatus for cup loading and unloading. The apparatus for cup loading and unloading is configured to load and unload the reaction cup 100 in the thromboelastography machine. The reaction cup 100 includes an inner cup 101 and an outer cup 102.

Figure 1:
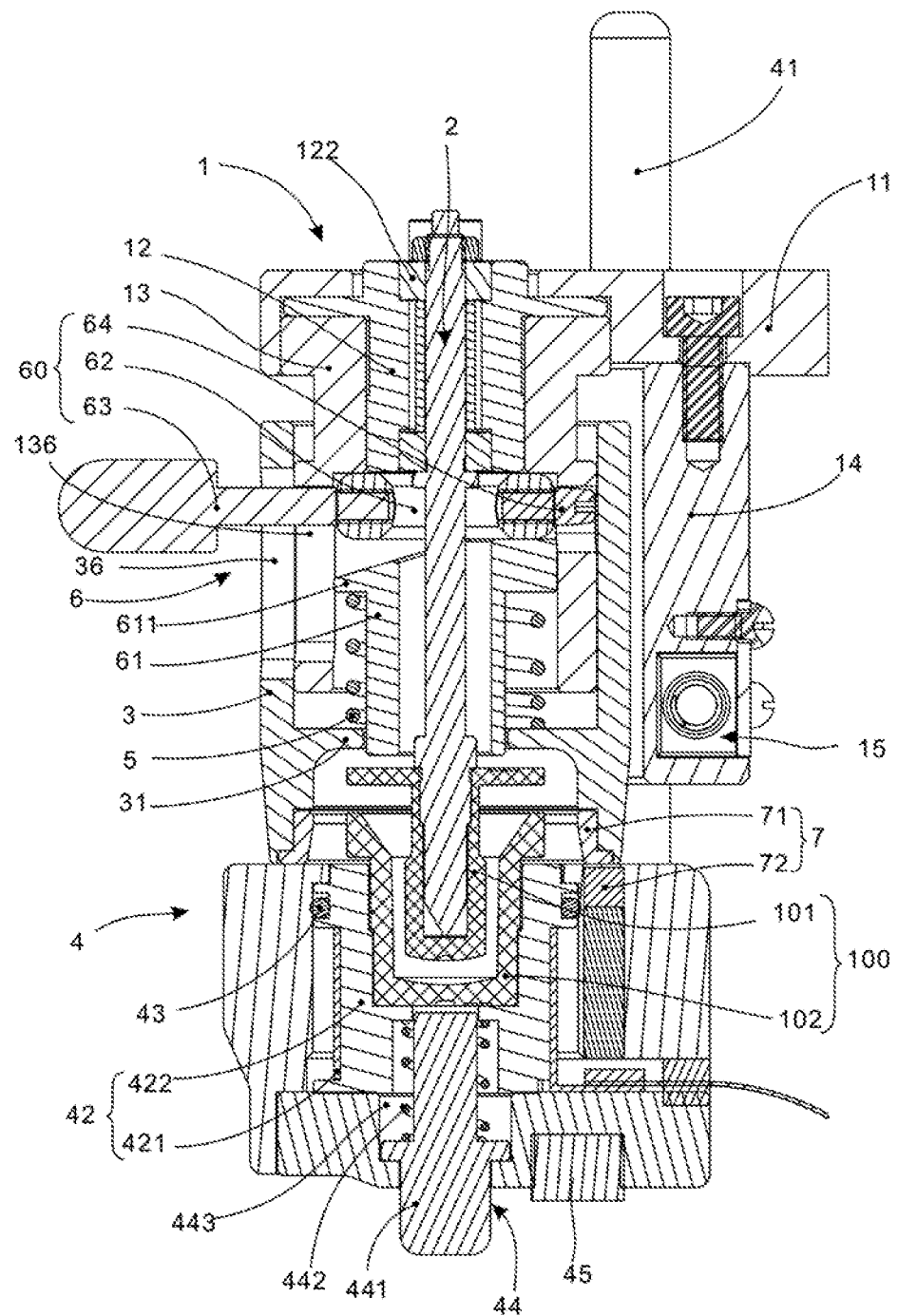
FIG. 1 is a cross-sectional structural view illustrating an apparatus for cup loading and unloading according to an implementation of the present disclosure.
Figure 2:
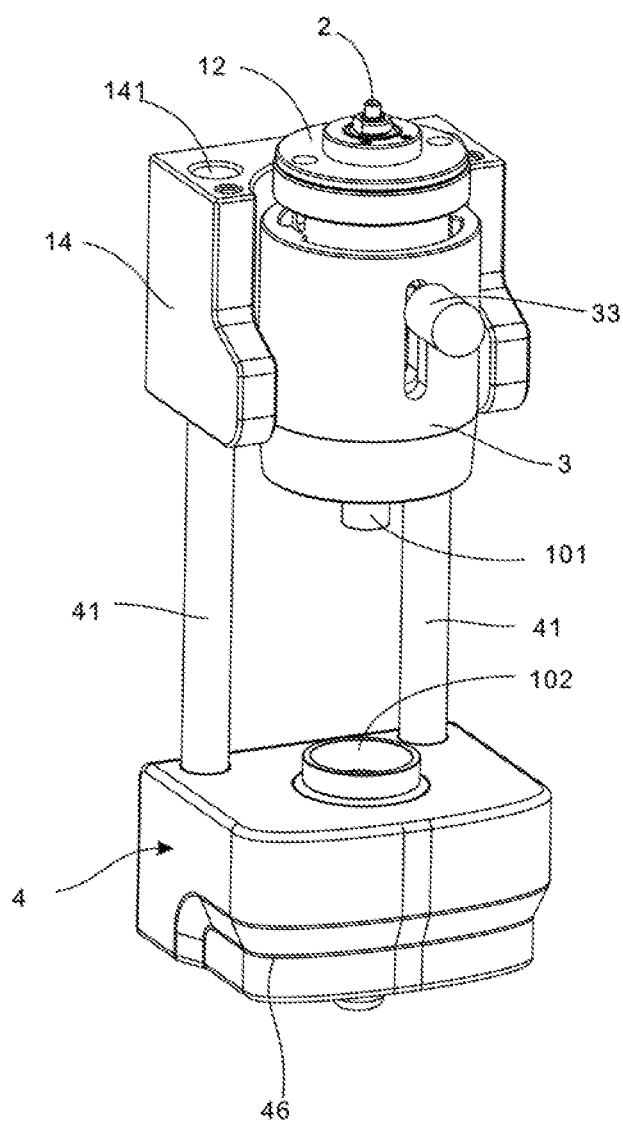
FIG. 2 is a schematic structural view illustrating a cup holder of the apparatus for cup loading and unloading of FIG. 1 at a lower position.
Figure 3:
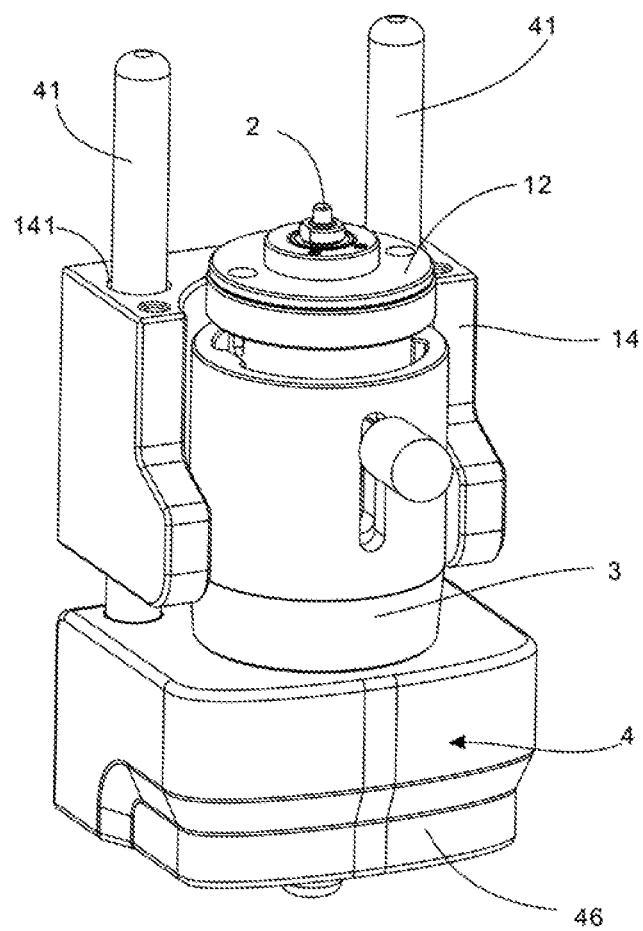
FIG. 3 is a schematic structural view illustrating a cup holder of the apparatus for cup loading and unloading of FIG. 1 at a higher position.

As illustrated in FIG. 1 to FIG. 3, the apparatus for cup loading and unloading includes a base 1, a shaft 2, a movable cover 3, and a cup holder 4. The base 1 may be fixed to a main body of the thromboelastography machine, so as to install the entire apparatus for cup loading and unloading in the thromboelastography machine. The shaft 2 is configured to engage with the inner cup 101. The cup holder 4 is configured to engage with the outer cup 102. During a reaction test, the movable cover 3 is configured to keep a certain gap between the inner cup 101 and the outer cup 102 for facilitating the reaction test.

The shaft 2 is rotatably connected to the base 1 about an axis of the shaft 2. The shaft 2 has an end configured to engage with the inner cup 101, so as to fix the inner cup 101 to the end of the shaft 2. The shaft 2 is usually arranged vertically, that is, the axis of the shaft 2 is parallel to the vertical direction. When the shaft 2 rotates, the inner cup 101 can be forced to rotate, such that the inner cup 101 rotates relative to the outer cup 102, thereby facilitating the reaction test of elastic properties of blood received in the outer cup 102.

The movable cover 3 is disposed around the shaft 2 and slidably connected to the base 1 along the axis of the shaft 2. The movable cover 3 is provided with an elastic member 5 therein. The cup holder 4 is slidably connected to the base 1 along the axis of the shaft 2 and disposed below the base 1 and the shaft 2. The cup holder 4 has a cavity (not shown) configured to engage with the outer cup 102, and the cavity has an open directed upward. After loading, the outer cup 102 is fixed in the cavity, so that the outer cup 102 is fixed relative to the cup holder 4. The cup holder 4 is slidably connected to the base 1, such that the cup holder 4 and the base 1 can move close to or away from each other.

In the process of loading the reaction cup 100, the inner cup 101 is supported within the outer cup 102, the outer cup 102 is supported within the cavity of the cup holder 4, and then the cup holder 4 can be pushed upward. When the cup holder 4 slides upward to a contact position (that is, the cup holder 4 is firstly not in contact with the movable cover 3, and then slides upward to contact with the movable cover 3), the cup holder 4 is in contact with a bottom end of the movable cover 3, and an upward movement of the cup holder 4 drives the movable cover 3 to slide upward, and the elastic member 5 is configured to provide a downward force to the movable cover 3 when in a deformation state. An approach movement between the end of the shaft 2 and the cup holder 4 is configured to generate a force to engage the inner cup 101 with the end of the shaft 2 and to engage the outer cup 102 within the cavity of the cup holder 4. Since the movable cover 3 can be forced to move upward, the cup holder 4 can get closer to the shaft 2 when moving upward. Consequently, the force between the cup holder 4 and the rotating shaft 2 enables the inner cup 101 and the outer cup 102 to engage at corresponding positions simultaneously. After loading of the reaction cup 100 is completed, an external force acting on the cup holder 4 is removed, and the movable cover 3 can slide downward under a force of the elastic member 5 to push the cup holder 4 downward, so as to keep a certain gap between the outer cup 102 and the inner cup 101, thereby facilitating the reaction test.

When pushing up the cup holder 4, the movable cover 3 is forced to move upward, and the cup holder 4 and the shaft 2 are forced to move toward each other, so as to provide a force to engage the inner cup 101 with the end of the shaft 2 and to engage the outer cup 102 within the cavity of the cup holder 4. Thus, the loading of the inner cup 101 and the outer cup 102 can be completed at one time. After loading, the movable cover 3 slides downward under the force of the elastic member 5, so as to push down the cup holder 4 to the test position. The steps for loading can be simplified, thereby facilitating operations. During the loading, there is no direct contact between the user and the reaction cup, thereby avoiding contamination of the reaction cup and ensuring the accuracy of test results.

The apparatus for cup loading and unloading further includes a cup ejection assembly 6. The cup ejection assembly 6 includes an ejection driving mechanism 60 and an ejection block 61. The ejection block 61 is slidably connected to the shaft 20 along the axis of the shaft 20. The ejection driving mechanism 60 is disposed between the base 1 and the ejection block 61 and configured to provide a downward force on the ejection block 61. The elastic member 5 is disposed between the ejection block 61 and the movable cover 3. The elastic member 5 may provide an upward force on the ejection block 61 when in a deformation state.

The elastic member 5 can simultaneously apply an elastic force to the ejection block 61 and the movable cover 3, thereby simplifying the structure, reducing the difficulty of assembly, and reducing the cost. In addition, in other implementations, there can be provided with two elastic members. One of the two elastic members may be disposed between the movable cover 3 and the base 1, and the other may be disposed between the ejection block 61 and the base 1. The two elastic members are configured to provide forces to the movable cover 3 and the ejection block 61.

In this implementation, the ejection block 61 is sleeved on the shaft 2, the elastic member 5 is configured as a compression spring and sleeved on the ejection block 61. The elastic member 5 and the ejection block 61 are disposed within the movable cover 3. The ejection block 61 has an ejection flange 611 disposed around a top portion of the ejection block 61. The movable cover 3 has an annular flange 31 circumferentially disposed on an inner wall of the movable cover 3. The ejection flange 611 is disposed above the annular flange 31. The elastic member 5 has an end abutted against the ejection flange 611 and another end abutted against the annular flange 31. The ejection flange 611 and the annular flange 31 are used to facilitate the assembly of the elastic member 5, and forces can be simultaneously supplied to the movable cover 3 and the ejection block 61. When the ejection block 61 is in a downward movement relative to the shaft 2, a bottom portion of the ejection block 61 is configured to move to pass through the annular flange 31 to a position below the annular flange, such that the bottom portion of the ejection block 61 abuts against the inner cup 101, and thus the ejection block 61 provides a downward force to the inner cup 101 to eject from the shaft 2, thereby completing the unloading of the inner cup 101.

In order to facilitate connection between the base 1 and components such as the shaft 2, the movable cover 3, and the ejection block 61, the base 1 is provided with a fixed substrate 11, a fixed member 12, a fixed cover 13, and a damper stop support 14. The fixed substrate 11 may be configured to fix the main body of the thromboelastography machine, so as to install the entire base 1 to the thromboelastography machine. The fixed member 12 is fixed to the fixed substrate 11. The fixed member 12 has a through hole, through which the shaft 2 is disposed and rotatably connected to the fixed member 12 about the axis of the shaft 2, so as to enable the shaft 2 to be rotatably fitted with the base 1. There may be provided with a bearing 122 between the fixed member 12 and the shaft 2 to ensure stability of rotation of the shaft 2.

The fixed cover 13 is fixed to the fixed member 12 and sleeved on the shaft 2. The ejection block 61 is sleeved between the fixed cover 13 and the shaft 2. The ejection block 61 is slidably engaged with the fixed cover 13 to achieve vertical sliding movement of the ejection block 61 relative to the shaft 2 and the base 1. The movable cover 3 is sleeved on the fixed cover 13, and the movable cover 3 is slidably engaged with the fixed cover 13 to achieve vertical sliding movement of the movable cover 3 relative to the base 1. The elastic member 5 can be sleeved between the ejection block 61 and the fixed cover 13. The cup ejection assembly 6 and the movable cover 3 can be assembled together by the fixed cover 13.

The ejection driving mechanism 60 includes a pin shaft 64, an ejection ring 62, and an ejection rod 63. The ejection ring 62 is sleeved on the shaft 2 and disposed between the ejection block 61 and the fixed member 12. The ejection ring 62 is rotatably connected to the fixed cover 13 via the pin shaft 64. The ejection rod 63 has an end fixedly connected to the ejection ring 62. The ejection rod 63 is disposed at one side of the shaft 2 and the pin shaft 64 is disposed at the other side, that is, the ejection rod 63 and the pin shaft 64 are installed opposite to each other. The fixed cover 13 has a first strip-shaped hole 136. The movable cover 3 has a second strip-shaped hole 36. The first strip-shaped hole 136 and the second strip-shaped hole 36 are disposed opposite to each other and extend along the axis of the shaft 2. The ejection rod 63 extends through the first strip-shaped hole 136 and the second strip-shaped hole 36, and has another end is disposed outside the movable cover 3. During ejecting, the another end of the ejection rod 63 is dialed down, and the ejection ring 62 is forced to rotate and tilt, so as to press the ejection block 61 downward, so that the ejection block 61 is forced to move down to generate a downward force to the inner cup 101. In order to facilitate the engagement between the ejection block 61 and the ejection ring 62, a top surface of the ejection block 61 is inclined.

A magnetic assembly 7 is disposed between the cup holder 4 and the movable cover 3. The magnetic assembly 7 includes a first magnetic element 71 and a second magnetic element 72. The first magnetic element 71 is fixedly connected to the cup holder 4. The second magnetic element 72 is fixedly connected to the bottom end of the movable cover 3. The first magnetic element 71 and the second magnetic element 72 are attracted each other in a process of the cup holder 4 and the movable cover 3 approaching each other. With cooperation of the first magnetic element 71 and the second magnetic element 72, the cup holder 4 and the movable cover 3 can be held at positions where they are in contact with each other. After the loading of the reaction cup 100 is completed, the cup holder 4 is forced to move downward, and the cup holder 4 and the movable cover 3 will not be separated from each other due to a magnetic attraction therebetween. At this time, a pre-determined gap can be kept between the inner cup 101 and the outer cup 102, that is, the cup holder 4 can be automatically positioned in the test position for testing. Therefore, the cup holder 4 is prevented from moving downward under its own gravity, thereby avoiding a gap between the inner cup 101 and the outer cup 102 being too large to avoid affecting the test effect.

In the implementation, the first magnetic element 71 is made of a ferrous material. The first magnetic element 71 is in an annular shape and embedded in an inner side of the bottom end of the movable cover 3 to facilitate assembly connection between the first magnetic element 71 and the movable cover 3. The second magnetic element 72 is a magnet fixed on an upper surface of the cup holder 4 for magnetic attraction with the first magnetic element 71. In other implementations, the first magnetic element 71 may also be a magnet, and the second magnetic element 72 may be made of a ferrous material. Alternatively, both the first magnetic element 71 and the second magnetic element 72 are magnets. The first magnetic element 71 and the second magnetic element 72 may also be fixed at other positions of the movable cover 3 and the cup holder 4, as long as the two magnetic elements can be attracted to each other and the movable cover 3 and the cup holder 4 can be relatively fixed.

The cup holder 4 is fixedly provided with a guiding rod 41 in parallel with the shaft 2. The base 1 has a guiding hole 141, and the guiding rod 41 is slidably disposed through the guiding hole 141. A damper stop mechanism 15 is disposed between the base 1 and the guiding rod 41 to allow the base 1 and the guiding rod 41 to be relatively fixed. With cooperation of the guiding rod 41 and the guiding hole 141, the base 1 and the cup holder 4 can move relative to each other, so that the two can move toward to or away from each other.

In one implementation, the damper stop support 14 of the base 1 has the guiding hole 141. The damper stop support 14 is fixed to the fixed substrate 11. The damper stop support 14 is used for connection with the guiding rod 41 in assembly. The damper stop mechanism 15 is disposed in the damper stop support 14. With the damper stop mechanism 15, when the external force acting on the cup holder 4 is removed, the base 1 and the guiding rod 41 can be relatively fixed, so that the base 1 and the cup holder 4 can be relatively fixed. In this way, the cup holder 4 can be hovered at any position to facilitate addition of a test blood sample into the outer cup 102 supported in the cup holder 4, which is convenient to use.

In addition, in other implementations, the guiding hold 141 can be defined in the cup holder 4 and the guiding rod 41 can be fixed to the base 1. The guiding rod 41 slides through the guiding hole 141. In this way, the relative sliding movement between the fixing seat 1 and the cup holder 4 can also be realized. The damper stop mechanism 15 can be disposed between the cup holder 4 and the guiding rod 41.

Figure 4:
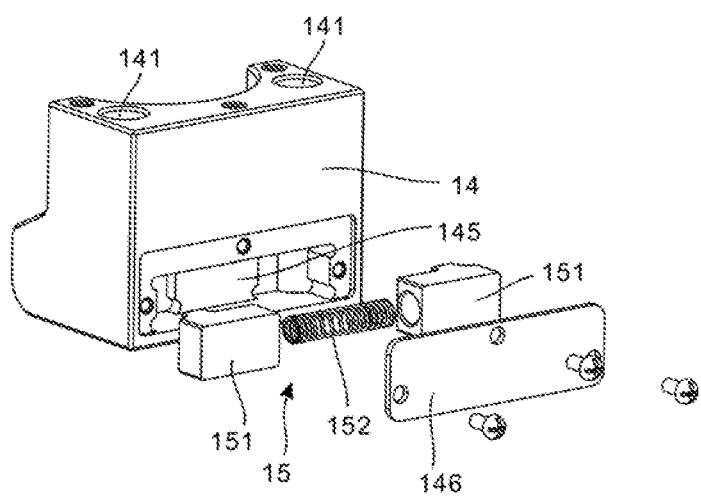
FIG. 4 is a schematic exploded view illustrating a damper stop mechanism of the apparatus for cup loading and unloading of FIG. 1.

As illustrated in FIG. 4, the damper stop mechanism 15 includes a locking block 151 and a locking spring 152. The locking block 151 is slidably disposed in the base 1, and is slidably movable in a direction perpendicular to an axis of the guiding rod 41. The locking spring 152 is connected to the locking block 151 and provides an elastic force on the locking block 151, whereby the locking block 151 is abutted against the guiding rod 41. With cooperation of the locking block 151 and the locking spring 152, the locking block 151 can provide the elastic force on the guiding rod 41 to affect the relative sliding movement between the guiding rod 41 and the base 1, so that the guiding rod 41 and the base 1 can be relatively fixed, and thus hovering the cup holder 4. The locking block 151 and the locking spring 152 form a prismatic pair. The locking block 151 generates a constant pressure on the guiding rod 41 under an action of the locking spring 152, thereby pressing the guiding rod 41, so that the cup holder 4 can be hovered at any position. At the same time, the guiding rod 41 can move smoothly in the damper stop support 14. In another implementation, the damper stop mechanism 15 may be provided with an elastic body mounted on the guiding rod 41 or the damper stop support 14 to generate a certain force to achieve hovering. There are other implementations of the damper stop mechanism 15, which are not described herein.

The base 1 has a damper stop groove 145 configured to facilitate an installation of the damper stop mechanism 15. The damper stop mechanism 15 can be disposed within the damper stop groove 145. The damper stop groove 145 is in intercommunication with the guiding hole 141, so that the locking block 151 can be abutted against the guiding rod 41 received in the guiding hole 141. The damper stop groove 145 can be correspondingly defined in the damper stop support 14 of the base 1. The damper stop support 14 is also provided with a pressing plate 146. The pressing plate 146 is secured to the damper stop groove 145 to limit the damper stop mechanism 15 within the damper stop groove 145.

The guiding rod 41 includes two guiding rods disposed in parallel to and spaced apart from each other. The locking block 151 includes two locking blocks 151. The locking spring 152 is configured as a compression spring. The locking spring 152 has two ends abutted against the two locking blocks 151 to provide a repulsive force on the two locking blocks 151, whereby each of the two locking blocks 151 is abutted against one of the two guiding rods 41. With the two guiding rods 41, the stability of the relative sliding movement between the cup holder 4 and the base 1 can be effectively ensured. With the engagement between the two locking blocks 151 and the two guiding rods 41, hovering control of the cup holder 4 can be realized. In addition, in other implementations, there can also be one guiding rod 41. In this case, the locking spring 152 has one end connected to the base 1 and another end connected to the locking block 151, so as to provide an elastic force on the locking block 151.

As illustrated in FIG. 1, the cup holder 4 is provided with a thermostat assembly 42 configured to keep the outer cup 102 at a constant temperature. The thermostat assembly 42 includes a heater 421 and a heating member 422. The heater 421 is disposed around the heating member 422. The cavity is defined in the heating member. The heater 421 is integrated with a temperature sensor and a temperature protection switch. With the thermostat assembly 42, a temperature of the outer cup 102 in the cavity can be kept constant during the reaction test, so that the accuracy of the reaction test can be improved.

The thromboelastography machine is primarily used for testing dynamic changes in a blood coagulation process, while the blood coagulation process is sensitive to temperature. In a case that parameters in the reaction test other than temperature are constant, the blood coagulation rate will be slow when the temperature is lower; on the contrary, a high temperature will promote the coagulation process. In order to simulate the real blood coagulation process of blood in the human body, a reaction temperature inside the reaction cup 100 during the reaction test of the thromboelastography machine needs to be as close as possible to normal human body temperature, which is usually taken as 37° C.

The heater 421 is affixed to the heating member 422, and a peripheral portion of the heater 421 is wrapped with a flexible material such as a heat shrink sleeve or a rubber holster, so as to ensure sufficient fit between the heater 421 and the heating member 422 in the cup holder 4, and to prevent the heater 421 from being separated from the heating member 422 or generating a gap with the heating member 422 after being used for a long period of time.

The heating member 422 is disposed in the cup holder 4. A flexible material element such as a sealing ring 43 is disposed between the heating member 422 and the cup holder 4. In this way, liquid that accidentally escapes from the reaction cup 100 will not flow through a gap between the heating member 422 and the cup holder 4 to the interior of the base 1, thereby avoiding a short-circuit risk of terminals of the heater 421.

The cup holder 4 is further provided with a pushrod mechanism 44 configured to eject the outer cup 102 from the cavity. The pushrod mechanism 44 includes a pushrod 441 and a pushrod spring 442. The cup holder 4 has a pushrod hole 443 extending through a bottom surface of the cup holder 4 and the cavity. The pushrod 441 is disposed slidably through the pushrod hole 443 along the axis of the shaft 2. The pushrod 441 has a top portion abutted against the outer cup 102, and a bottom portion extending outside the pushrod hole 443 and projecting from the bottom surface of the cup holder 4. The pushrod spring 442 is connected to the pushrod 441 and is configured to provide a downward force on the pushrod 441.

The pushrod 441 and the cup holder 4 may form a prismatic pair therebetween. The pushrod 441 may be reset automatically under the action of the pushrod spring 442, such that the bottom portion of the pushrod 441 projects from the bottom surface of the cup holder 4. When the reaction test is finished, the cup holder 4 is forced to move downward, so as to move the pushrod 441 upward to retract into the cup holder 4. The top portion of the pushrod 441 moves back into the cavity and abuts against the outer cup 102, and then the outer cup 102 is forced to move upward. Thus, unloading of the outer cup 102 of the reaction cup 100 is completed. In the implementation, the pushrod spring 442 is configured as a compression spring disposed between the pushrod 441 and the cup holder 4. In other implementations, the pushrod spring 442 can also be configured as a torsion spring, a tension spring, or the like.

A cushion 45 is disposed in a bottom portion of the cup holder 4. The cushion 45 is configured to contact with a structure below the cup holder 4 before the cup holder 4. The cushion 45 can be protruded from or embedded into the cup holder 4. The cushion 45 can also be fixed in the structure below the cup holder 4. The function of the cushion 45 is to reduce noise during the unloading of the outer cup 102 of the reaction cup 100, and more importantly, to effectively reduce vibration of the machine caused by the unloading of the outer cup 102 of the reaction cup 100.

The cup holder 4 is further provided with a recess 46. The recess 46 is disposed along a part of edge of the bottom portion of the cup holder 4. The recess 46 can be used to facilitate the user to apply force to the cup holder 4 to move the cup holder upward.

The above implementations do not constitute any limitation on the scope of the technical solutions. Any modifications, equivalent substitutions, and improvements made within the spirit and principles of the above-described implementations are intended to be included within the scope of the present disclosure.

What is claimed is:

1. An apparatus for cup loading and unloading, comprising:
   a base;
   a shaft, rotatably connected to the base about an axis of the shaft and having an end configured to engage with an inner cup;
   a movable cover, disposed around the shaft and slidably connected to the base along the axis of the shaft, the movable cover being provided with an elastic member therein;
   a cup holder, slidably connected to the base along the axis of the shaft and disposed below the base and the shaft, the cup holder having a cavity configured to engage with an outer cup, and the cavity having an opening directed upward;
   a cup ejection assembly, comprising an ejection driving mechanism and an ejection block, the ejection block being slidably connected to the shaft along the axis of the shaft, the ejection driving mechanism being disposed between the base and the ejection block and configured to provide a downward force on the ejection block, and the elastic member being disposed between the ejection block and the movable cover and configured to provide an upward force on the ejection block when in a deformation state; and
   wherein, when the cup holder slides upward to a contact position, the cup holder is in contact with a bottom end of the movable cover, and an upward movement of the cup holder drives the movable cover to slide upward;
   the elastic member is configured to provide a downward force on the movable cover when in a deformation state; and
   an approach movement between the end of the shaft and the cup holder is configured to generate a force to engage the inner cup with the end of the shaft and to engage the outer cup within the cavity of the cup holder.

2. The apparatus of claim 1, wherein:
   the ejection block is sleeved on the shaft, the elastic member is configured as a compression spring and sleeved on the ejection block, and the elastic member and the ejection block are disposed within the movable cover;
   the ejection block has an ejection flange disposed around a top portion of the ejection block, the movable cover has an annular flange circumferentially disposed on an inner wall of the movable cover, the ejection flange is disposed above the annular flange, and the elastic member has an end abutted against the ejection flange and another end abutted against the annular flange; and
   a bottom portion of the ejection block is configured to move to pass through the annular flange to a position below the annular flange, when the ejection block is in a downward movement relative to the shaft.

3. The apparatus of claim 1, further comprising a magnetic assembly, wherein the magnetic assembly comprises a first magnetic element fixedly connected to the cup holder and a second magnetic element fixedly connected to the bottom end of the movable cover, and the first magnetic element and the second magnetic element are attracted to each other in a process of the cup holder and the movable cover approaching each other.

4. The apparatus of claim 1, wherein:
   the cup holder is fixedly provided with a guiding rod in parallel with the shaft;
   the base has a guiding hole, and the guiding rod is slidably disposed through the guiding hole; and
   a damper stop mechanism is disposed between the base and the guiding rod to allow the base and the guiding rod to be relatively fixed.

5. The apparatus of claim 4, wherein:
   the damper stop mechanism comprises a locking block and a locking spring;
   the locking block is slidably disposed in the base, and is slidably movable in a direction perpendicular to an axis of the guiding rod; and the locking spring is connected to the locking block and provides an elastic force on the locking block, whereby the locking block is abutted against the guiding rod.

6. The apparatus of claim 5, wherein:
the guiding rod comprises two guiding rods disposed in parallel to and spaced apart from each other;
the locking block comprises two locking elements;
the locking spring is configured as a compression spring; and
the locking spring has two ends, each end abutted against one of the two locking elements to provide a repulsive force on the two locking elements, whereby each of the two locking elements is abutted against one of the two guiding rods.

7. The apparatus of claim 1, wherein:
the cup holder is provided with a thermostat assembly configured to keep the outer cup at a constant temperature;
the thermostat assembly comprises a heater and a heating member, the heater being disposed around the heating member, and the cavity being defined in the heating member; and
the heater is integrated with a temperature sensor and a temperature protection switch.

8. The apparatus of claim 1, wherein:
the cup holder is further provided with a pushrod mechanism configured to eject the outer cup from the cavity;
the pushrod mechanism comprises a pushrod and a pushrod spring;
the cup holder has a pushrod hole extending through a bottom surface of the cup holder and the cavity;
the pushrod is slidably disposed through the pushrod hole along the axis of the shaft;
the pushrod has a top portion configured to abut against the outer cup, and a bottom portion extending outside the pushrod hole and projecting from the bottom surface of the cup holder; and
the pushrod spring is connected to the pushrod and is configured to provide a downward force on the pushrod.

9. The apparatus of claim 1, wherein the base is provided with a fixed substrate, a fixed member fixed to the fixed substrate, a fixed cover fixed to the fixed member and sleeved on the shaft, and a damper stop support fixed to the fixed substrate.

10. The apparatus of claim 9, wherein the ejection driving mechanism comprises a pin shaft, an ejection ring, and an ejection rod, the ejection ring being sleeved on the shaft and disposed between the ejection block and the fixed member, the ejection ring being rotatably connected to the fixed cover via the pin shaft, and the ejection rod having an end fixedly connected to the ejection ring and another end disposed outside the movable cover.

11. The apparatus of claim 10, wherein the fixed cover has a first strip-shaped hole, the movable cover has a second strip-shaped hole, and the ejection rod extends through the first strip-shaped hole and the second strip-shaped hole.

12. The apparatus of claim 11, wherein the ejection block has a top surface which is inclined.

13. A thromboelastography machine, comprising an apparatus for cup loading and unloading, wherein the apparatus comprises:
a base;
a shaft, rotatably connected to the base about an axis of the shaft and having an end configured to engage with an inner cup;
a movable cover, disposed around the shaft and slidably connected to the base along the axis of the shaft, the movable cover being provided with an elastic member therein;
a cup holder, slidably connected to the base along the axis of the shaft and disposed below the base and the shaft, the cup holder having a cavity configured to engage with an outer cup, and the cavity having an opening directed upward, wherein the cup holder is provided with a thermostat assembly comprising a heater and a heating member configured to keep the outer cup at a constant temperature;
a cup ejection assembly, comprising an ejection driving mechanism and an ejection block, the ejection block being slidably connected to the shaft along the axis of the shaft, the ejection driving mechanism being disposed between the base and the ejection block and configured to provide a downward force on the ejection block, and the elastic member being disposed between the ejection block and the movable cover and configured to provide an upward force on the ejection block when in a deformation state; and
wherein, when the cup holder slides upward to a contact position, the cup holder is in contact with a bottom end of the movable cover, and an upward movement of the cup holder drives the movable cover to slide upward;
the elastic member is configured to provide a downward force on the movable cover when in a deformation state; and
an approach movement between the end of the shaft and the cup holder is configured to generate a force to engage the inner cup with the end of the shaft and to engage the outer cup within the cavity of the cup holder.

14. The thromboelastography machine of claim 13, wherein:
the ejection block is sleeved on the shaft, the elastic member is configured as a compression spring and sleeved on the ejection block, and the elastic member and the ejection block are disposed within the movable cover;
the ejection block has an ejection flange disposed around a top portion of the ejection block, the movable cover has an annular flange circumferentially disposed on an inner wall of the movable cover, the ejection flange is disposed above the annular flange, and the elastic member has an end abutted against the ejection flange and another end abutted against the annular flange; and
a bottom portion of the ejection block is configured to move to pass through the annular flange to a position below the annular flange, when the ejection block is in a downward movement relative to the shaft.

15. The thromboelastography machine of claim 13, further comprising a magnetic assembly, wherein the magnetic assembly comprises a first magnetic element fixedly connected to the cup holder and a second magnetic element fixedly connected to the bottom end of the movable cover, and the first magnetic element and the second magnetic element are attracted to each other in a process of the cup holder and the movable cover approaching each other.

16. The thromboelastography machine of claim 13, wherein:
the cup holder is fixedly provided with a guiding rod in parallel with the shaft;
the base has a guiding hole, and the guiding rod is slidably disposed through the guiding hole; and a damper stop mechanism is disposed between the base and the guiding rod to allow the base and the guiding rod to be relatively fixed.

17. The thromboelastography machine of claim 15, wherein:
the damper stop mechanism comprises a locking block and a locking spring;
the locking block is slidably disposed in the base, and is slidably movable in a direction perpendicular to an axis of the guiding rod; and
the locking spring is connected to the locking block and provides an elastic force on the locking block, whereby the locking block is abutted against the guiding rod.

18. The thromboelastography machine of claim 16, wherein:
the guiding rod comprises two guiding rods disposed in parallel to and spaced apart from each other;
the locking block comprises two locking elements;
the locking spring is configured as a compression spring; and
the locking spring has two ends, each end abutted against one of the two locking elements to provide a repulsive force on the two locking elements, whereby each of the two locking elements is abutted against one of the two guiding rods.

19. The thromboelastography machine of claim 13, wherein:
the heater is disposed around the heating member, and the cavity is defined in the heating member; and
the heater is integrated with a temperature sensor and a temperature protection switch.

20. The thromboelastography machine of claim 13, wherein:
the cup holder is further provided with a pushrod mechanism configured to eject the outer cup from the cavity;
the pushrod mechanism comprises a pushrod and a pushrod spring;
the cup holder has a pushrod hole extending through a bottom surface of the cup holder and the cavity;
the pushrod is slidably disposed through the pushrod hole along the axis of the shaft;
the pushrod has a top portion configured to abut against the outer cup, and a bottom portion extending outside the pushrod hole and projecting from the bottom surface of the cup holder; and
the pushrod spring is connected to the pushrod and is configured to provide a downward force on the pushrod.

21. The thromboelastography machine of claim 13, wherein:
the base is provided with a fixed substrate, a fixed member fixed to the fixed substrate, a fixed cover fixed to the fixed member and sleeved on the shaft, and a damper stop support fixed to the fixed substrate, and
the ejection driving mechanism comprises a pin shaft, an ejection ring, and an ejection rod, the ejection ring being sleeved on the shaft and disposed between the ejection block and the fixed member, the ejection ring being rotatably connected to the fixed cover via the pin shaft, and the ejection rod having an end fixedly connected to the ejection ring and another end disposed outside the movable cover.

\* \* \* \* \*